United States Patent [19]

Lyall

[11] Patent Number: 4,596,246
[45] Date of Patent: Jun. 24, 1986

[54] METHOD AND APPARATUS FOR CONVERTING PATIENT BREATHING SYSTEM BETWEEN CIRCLE AND NON-REBREATHING CONFIGURATIONS

[76] Inventor: Robert N. Lyall, 668 Falkland Road, Victoria, British Columbia, Canada, V8S 4L5

[21] Appl. No.: 583,226

[22] Filed: Feb. 24, 1984

[51] Int. Cl.$^4$ ............................................. A61M 16/00
[52] U.S. Cl. ........................... 128/202.27; 128/203.28; 128/911; 128/205.12
[58] Field of Search .................. 128/204.18, 205.14, 128/205.15, 205.12, 205.17, 205.24, 202.27, 911

[56] References Cited

U.S. PATENT DOCUMENTS

| | | | |
|---|---|---|---|
| 2,969,789 | 1/1961 | Morch | 128/205.14 |
| 3,021,840 | 2/1962 | Hallamore et al. | 128/204.14 |
| 3,721,239 | 3/1973 | Myers | 128/911 |
| 3,901,230 | 8/1975 | Henkin | 128/205.17 |
| 4,007,737 | 2/1977 | Paluch | 128/911 |
| 4,069,818 | 1/1978 | Schreiber | 128/205.15 |
| 4,224,940 | 9/1980 | Monnier | 128/205.16 |
| 4,265,235 | 5/1981 | Fukunaga | 128/205.12 |
| 4,320,754 | 3/1982 | Watson et al. | 128/911 |

FOREIGN PATENT DOCUMENTS 3313855 3/1984 Fed. Rep. of Germany ................... 128/204.25

OTHER PUBLICATIONS

"MediPlast", Brochure Describing a Coax 2 Anaesthesia System.

*Primary Examiner*—Henry J. Recla
*Attorney, Agent, or Firm*—Klarquist, Sparkman, Campbell, Leigh & Whinston

[57] ABSTRACT

An adaptor for converting patient breathing apparatus from the "circle" to the Bain circuit configuration. The adaptor facilitates rapid conversion of the patient breathing circuit without necessitating duplication of breathing circuit components and without the need for an expensive Bain circuit mount. The adaptor substantially reduces the complexity of the conversion operation, thereby minimizing the possibility that an erroneous circuit may be established with the attendant possibility for patient injury.

6 Claims, 4 Drawing Figures

METHOD AND APPARATUS FOR CONVERTING PATIENT BREATHING SYSTEM BETWEEN CIRCLE AND NON-REBREATHING CONFIGURATIONS

FIELD OF THE INVENTION

This application pertains to anesthetic machines and circuitry and, in particular, to an adaptor for converting such apparatus from the "circle" to the "Bain circuit" configuration.

BACKGROUND OF THE INVENTION

Medical equipment herein termed "patient breathing apparatus" is used to deliver oxygen with anesthetic gases and vapours ("breathing gas") to a patient while surgical procedures are performed on the patient. Usually, such apparatus provides a mixture of oxygen, with or without nitrous oxide, for inspiration by the patient, and may conventionally include controls for either assisting or controlling breathing, exhaled volume indicators, alarm systems, positive end expiratory pressure ("PEEP") valves, pressure indicators, gas concentration monitors, flow indicators, heated humidifiers for warming and humidifying the breathing gas and tubing for interconnecting these components with each other and with the patient, thereby forming a "patient breathing circuit". Often, the anesthetist who monitors and controls the apparatus must add specific ancilliary devices and accessories to the patient breathing circuit, as warranted by factors such as the physiological status of the patient, the nature of the surgical procedure, the anesthetic technique employed, etc.

Traditionally, patient breathing circuits have adopted the so-called "circle" configuration in which breathing gas delivered to the patient is substantially constrained, by a pair of one-way valves, to flow in one direction around a circuitous path. The gas flows through an inspiratory hose or "channel", into the patient's lungs and is then returned, after expiry by the patient, through an expiratory channel (another hose), to a carbon dioxide absorber which removes carbon dioxide from the expired gas so that it may be re-cycled to the patient via the inspiratory channel. Periodically, (or continuously at low gas flow rates) fresh anesthetic or other gases may be introduced into the inspiratory channel, and some portion of the expired gas may be allowed to escape from the expiratory channel for collection by a scavenging device, rather than being returned to the patient.

Most anesthetic machines currently marketed are supplied by the manufacturer with fittings specifically adapted to the "circle" circuit configuration. However, the circle circuit configuration is not universally employed. For reasons hereinafter discussed in greater detail, anesthetists often change the configuration of anesthetic machines from the "circle" circuit to the so-called "Bain circuit" configuration.

The primary characteristic distinguishing the Bain circuit configuration from the circle circuit configuration is that, in the Bain circuit, the inspiratory and expiratory breathing hoses are coaxial, whereas they are series-connected in the circle circuit. In a typical Bain circuit, fresh gas is delivered through the innermost co-axial hose to the distal end of that hose, for inspiration by the patient. The outer, larger diameter hose, which surrounds the fresh gas delivery hose, serves as a fresh gas reservoir containing some fresh gas for inspiration by the patient, and as an expiratory channel for communicating gas exhaled by the patient to the exhaust/scavenging portion of the circuit. Further, in the Bain circuit, unlike the circle circuit, breathing gas does not flow unidirectionally around the circuit. Rather, the direction of gas flow in the Bain circuit reverses periodically as the patient inspires and expires breathing gas.

Heretofore, anesthetic machines supplied with fittings adapted to the circle circuit configuration have not been readily convertible to the Bain circuit configuration. Such conversion has heretofore required an expensive Bain circuit mount and has necessitated duplication of several circuit components (i.e. exhaust valves, connections to ventilators and to scavenging systems). The conversion procedure results in a profusion of tubing which is cumbersome and time consuming to interconnect. Further, the conversion procedure heretofore adopted is of such complexity that there is a significant potential that an error may be made during conversion from one configuration to another, with an attendant risk of patient injury.

The present invention provides an adaptor which facilitates rapid conversion of patient breathing apparatus between the circle and Bain circuit configuration. Such conversion obviates the need for an expensive Bain circuit mount, is accomplished without requiring expensive duplication of circuit components, and significantly reduces the complexity of the conversion operation, thereby minimizing the likelihood that a deficient patient breathing circuit may be configured, and accordingly minimizing the risk of patient injury.

SUMMARY OF THE INVENTION

In a broad aspect, the invention provides an adaptor for converting patient breathing apparatus from the circle circuit configuration to the Bain circuit configuration. The adaptor comprises a conduit for conveying gas exhaled by the patient through the Bain circuit expiratory channel to an outlet valve of the circle circuit and for returning gas emitted from an inlet valve of the circle circuit to the Bain circuit expiratory channel.

Advantageously a coupler is provided for connecting the anesthetic machine into the circle circuit or into the Bain circuit. A control valve in the circle circuit portion of the coupler is opened when the anesthetic machine is connected into the circle circuit, but closes when the anesthetic machine is disconnected from the circle circuit for connection into the Bain circuit via a mating coupler.

DESCRIPTION OF THE PREFERRED EMBODIMENT

I. Background

(a) Circle circuit configuration

Figure 1:
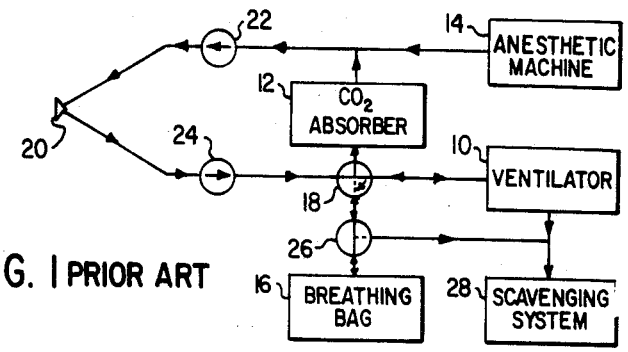
FIG. 1 is a block diagram showing the arrangement of basic components comprising a typical "circle" patient breathing circuit configuration.

FIG. 1 is a block diagram showing the arrangement of basic components typically included in a patient breathing circuit having the "circle" configuration. The circuit includes a ventilator 10 for controlling the flow of gas to and from the patient, a carbon dioxide ("$CO_2$") absorber 12 for removing carbon dioxide from that portion of the gas which is expired by the patient and which may be intentionally directed back to the patient for re-inhalation with fresh gas ($CO_2$ absorber 12 thus serves as a "gas source", since it may supply a large portion of the gas breathed by the patient), and an anesthetic machine 14 for supplying a desired mixture of fresh anaesthetic gases in sufficient quantity. Breathing bag 16 may be used instead of ventilator 10, in which case manually operated switch 18 facilitates disconnection of ventilator 10 from the circuit and connection of breathing bag 16 in its place. The circuit may also include a gas monitor for providing an indication of the concentration of a specific gas, a spirometer for providing an indication of the volume of gas passing through a portion of the patient breathing circuit, a pressure gauge for providing an indication of the instantaneous gas pressure, a positive end expiratory pressure ("PEEP") valve for preventing a return to zero pressure when the patient exhales and other components. However, such additional components are not essential to the presentation and are accordingly omitted to avoid obscuring details of the invention.

Hoses (represented in FIGS. 1, 2 and 3 by straight lines) connected between the breathing circuit components facilitate the flow of breathing gas to and from endotracheal tube connector 20 (which is inserted into the patient's endotracheal tube) and throughout the patient breathing circuit in the directions indicated by the arrows. One-way valves 22, 24 facilitate the flow of gas in the desired direction around the patient breathing circuit. Specifically, during inhalation, one-way "inlet" valve 22 permits gas flow into the inspiratory channel only in the direction of the arrow shown on valve 22; namely, from ventilator 10 (or breathing bag 16, depending upon the position of switch 18), $CO_2$ absorber 12 and anesthetic machine 14 to the patient. Similarly, during exhalation, one-way "outlet" valve 24 permits gas flow from the expiratory channel only in the direction of the arrow shown on valve 24; namely, from the patient to $CO_2$ absorber 12 and (again, depending upon the position of switch 18) to ventilator 10 or to breathing bag 16. A normally closed, pressure-activated exhaust valve 26, and a corresponding exhaust valve included in ventilator 10, but not shown in the drawings, allow exhaust gases to escape to scavenging system 28, which prevents the release into the atmosphere of anesthetic agents remaining in the expired gases. More particularly, as fresh anesthetic gas enters the circuit from anesthetic machine 14, the gas pressure in the circuit increases until exhaust valve 26 (or the exhaust valve in ventilator 10, depending upon the position of switch 18) opens and gas is displaced from the circuit to scavenging system 28 unti the gas pressure in the circuit drops sufficiently to allow valve 26 to close.

In operation, fresh gas is introduced into the breathing circuit by anesthetic machine 14, via valve 22 for patient inspiration via connector 20. During spontaneous respiration (i.e. when switch 18 is positioned to connect breathing bag 16 into the circuit) the patient withdraws gas from the circuit by inhaling, and a comparable volume of gas flows into the circuit from breathing bag 16 to equalize the circuit pressure. When the patient spontaneously exhales, gas passes through valve 24 into breathing bag 16. However, if the gas pressure in the circuit is sufficient to open valve 26 or the corresponding valve in ventilator 10 (which will periodically happen as anesthetic machine 14 introduces more fresh gas into the circuit) exhaled gas is displaced into scavenging system 28 until the gas pressure drops sufficiently to allow the exhaust valve to close. During positive pressure respiration (i.e. when switch 18 is positioned to connect ventilator 10 into the circuit) gas is forced into the patient's lungs (during inhalation) via $CO_2$ absorber 12 and valve 22, and withdrawn from the patient's lungs (during exhalation) via valve 24; valve 26 or the corresponding valve in ventilator 10 again permitting exhaled gases to escape to scavenging system 28 as fresh gases are introduced by anesthetic machine 14.

It can thus be seen that the circle circuit configuration derives its name from the fact that breathing gas supplied to the patient is constrained, by valves 22, 24 to flow continuously, in one direction, around a circuitous path from $CO_2$ absorber 12, through one-way valve 22 and through the inspiratory channel to the patient, and is then returned, after expiration by the patient, through the expiratory channel and through one-way valve 24, back to $CO_2$ absorber 12.

The circle configuration offers a number of advantages. First, since breathing gas may be continuously recycled to the patient, the circle configuration facilitates relatively economical usage of fresh anesthetic gases supplied by anesthetic machine 14 (some vaporizable agents used in anesthetic procedures are very costly). Second, the circle configuration facilitates relatively rapid patient rebreathing of a comparatively small volume of breathing gas, thereby enabling the patient's alveoli to quickly stabilize the temperature and humidity of the breathing gas and minimizing or eliminating the requirement for further humidification of the anesthetic gases which are dry when initially introduced into the patient breathing circuit. This is a significant advantage because heat and water may be lost through the patient's lungs if the breathing gas supplied to the patient is not heated and humidified to levels approximating conditions in the lung.

The circle configuration lends itself to use in procedures where the patient must be anesthetized for a relatively long time (i.e. for longer than about ½ hour) since the aforementioned advantages take on greater significance in lengthier procedures. More particularly, the aforementioned advantages are not typically obtained if the circle configuration is adopted for procedures of less than about ½ hour's duration. A finite time is required to purge the patient breathing circuit of gases present when the operation starts and to establish a steady state of gas concentration, gas temperature, gas humidity, etc. in the patient breathing circuit and in the patient. Relatively high fresh gas flow rates are required to purge the circuit and establish a steady state; the result being that a comparatively large quantity of expensive fresh gas must be supplied in the initial stages of the procedure, which tends to eliminate the possibility of economic advantage in a shorter procedure. Further, since the patient's alveoli cannot adequately heat and humidify large volumes of gas introduced over a short time span, external heaters and humidifiers may be required during the initial stages of the procedure to assist in establishing a steady state in the breathing circuit.

(b) Bain circuit configuration (Prior Art)

Figure 2:
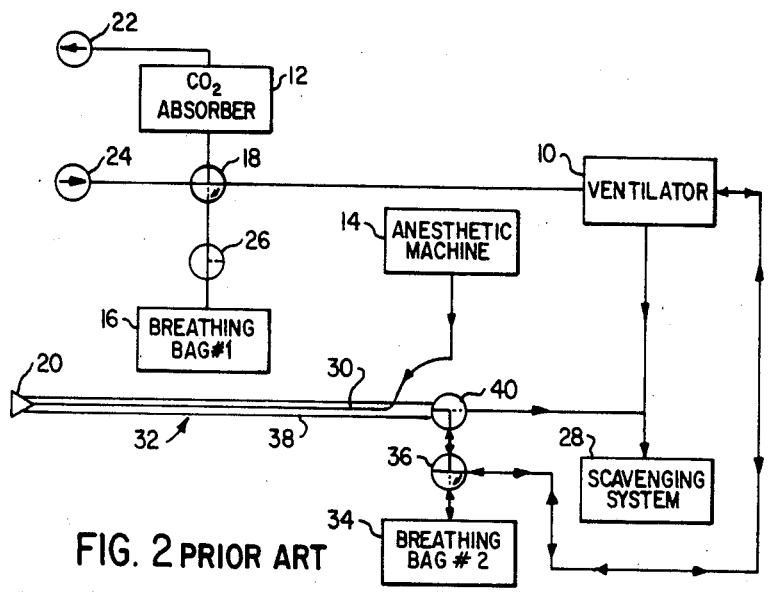
FIG. 2 is a block diagram showing how the circle configuration of FIG. 1 has heretofore been converted to the Bain circuit configuration.

FIG. 2 is a block diagram showing how the circle configuration of FIG. 1 has heretofore been converted to the "Bain circuit" configuration.

Ventilator 10, $CO_2$ absorber 12, breathing bag 16, switch 18, one way valves 22 and 24, exhaust valve 26 and scavenging system 28 remain configured essentially as described above with reference to the circle circuit, although only ventilator 10 plays an active role in the Bain circuit. Accordingly, arrows are not shown in FIG. 2 on lines which represent hoses interconnecting circuit components which function only in the circle circuit. The circle circuit inspiratory and expiratory breathing hoses are disconnected from one way valves 22 and 24. Anesthetic machine 14 is disconnected from the inlet port of one way valve 22 and reconnected to the inner (inspiratory) hose 30 of the coaxial Bain hose assembly 32. A second breathing bag 34 is provided, together with a second manually operated switch 36 for alternately switching ventilator 10 and breathing bag 34 into and out of the Bain circuit. The outer (expiratory) hose 38 of coaxial Bain hose assembly 32 is connected to an inlet port of a normally closed pressure-activated exhaust valve 40. (In practice, an expensive Bain circuit mount is purchased and attached to anesthetic machine 14. The mount—not shown—incorporates fittings for interconnecting breathing bag 34, hose 38 and valve 40.) Scavenging system 28 is disconnected from the outlet port of valve 26 and reconnected to the outlet port of valve 40. Gas expired by the patient normally passes through valve 40 to ventilator 10 or to breathing bag 34 (depending upon the position of switch 36). However, if the gas pressure in the Bain circuit is sufficient to open valve 40 or the corresponding valve in ventilator 10 (which will happen when anesthetic machine 14 introduces fresh gas into the circuit) exhaust gas is displaced into scavenging system 28 until the circuit pressure drops sufficiently to allow the exhaust valve to close.

In operation, fresh gas is introduced by anesthetic machine 14 into inner hose 30 for patient inspiration via endotracheal tube connector 20. In addition to providing an expiratory channel for removal of exhaust gases, outer hose 38 also serves, in the region near connector 20, as a conduit and "reservoir" for fresh gas which may also be inspired by the patient. During spontaneous respiration (i.e. when switch 36 is positioned to connect breathing bag 34 into the circuit) the patient, during inhalation, withdraws gas from the reservoir in hose 38 and gas flows into the circuit from breathing bag 34 (via switch 36 and valve 40) to equalize the pressure. During positive pressure respiration (i.e. when switch 36 is positioned to connect ventilator 10 into the circuit) ventilator 10 forces gas into the patient's lungs (during inhalation) through hose 38. Expiration is a passive event during both spontaneous and positive pressure respiration; outer hose 38 merely acting to convey exhaled gas from the patient to breathing bag 34 or ventilator 10, (again, depending upon the position of switch 36) or to scavenging system 28 if the circuit pressure is sufficient to open valve 40 or the corresponding valve in ventilator 10.

A principle advantage of the Bain circuit, over the circle circuit configuration, is that relatively little time is lost in purging the Bain circuit—almost as soon as the Bain circuit is activated a relatively high concentration of fresh breathing gas may be introduced directly into the patient's lungs. Thus, the Bain circuit is well suited for use in relatively short procedures. A further advantage of the Bain circuit is that it offers relatively low resistance to the patient's normal breathing, which renders it particularly useful in pediatric cases.

II. The Preferred Embodiment

Those skilled in the art will recognize that the circle circuit configuration is preferred in some anesthetic procedures, whereas the Bain circuit configuration is preferred in others. Thus, the patient breathing apparatus available in a typical operating theatre commonly undergoes a continual process of conversion and reconversion between the circle and Bain circuit configurations. Heretofore, such conversions have required an expensive Bain circuit mount to which the coaxial breathing hoses characterizing the Bain circuit are connected. As previously suggested, the standard circle circuit mounts (including one-way valves 22 and 24) provided on most commercially available anesthetic machines have been thought to necessitate duplication of many breathing circuit components such as breathing bags, exhaust hoses and valves, oxygen sensor fittings and the like, in order to facilitate arrangement of such components in the Bain configuration. A significant disadvantage of the Bain circuit configuration of FIG. 2 is that it precludes the use of switch 18 which is typically provided on commercially available circle circuit-adapted anesthetic machines. This causes considerable inconvenience to the presiding anesthetist which has heretofore only been overcome by providing a duplicate switch 36, thereby further complicating the Bain circuit of FIG. 2. It can thus be seen that the conversion of circle-circuit adapted breathing apparatus to the Bain circuit configuration is typically expensive and results in a profusion of components in the patient breathing circuit, significantly complicating the procedure required to configure the breathing circuit and thereby increasing the possibility that a defective breathing circuit having the possibility for causing patient injury may be established.

It is believed that the complexity inherent in the prior art procedure for converting patient breathing apparatus from the circle to the Bain circuit configuration has resulted from a perceived need to eliminate, throughout the breathing circuit, the unidirectional gas flow which characterizes the circle configuration, in order that the direction of gas flow may periodically reverse as the patient inspires and expires through the Bain circuit. The circle-to-Bain circuit adaptor of the preferred embodiment permits patient breathing apparatus to remain substantially in the circle configuration, even after conversion to the Bain configuration. As will be seen, the adaptor of the preferred embodiment facilitates establishment of a "mini circle circuit" which retains the basic configuration of FIG. 1, but to which the coaxial Bain circuit breathing hoses may be connected. In essence, the preferred embodiment circumvents the unidirectional flow characterizing the circle circuit, and permits pressure equalization in the Bain circuit during the various respiration phases, while retaining the essential configuration of the circle circuit. The preferred embodiment facilitates rapid, safe conversion between the circle and Bain configurations by minimizing changes to the circuitry and without requiring any expensive duplication of components.

In the preferred embodiment, the circle circuit configuration of FIG. 1 is converted to the Bain circuit configuration of FIG. 3 as follows:

(1) The circle circuit inspiratory and expiratory breathing hoses are disconnected from the outlet port of one-way valve 22 and from the inlet port of one-way valve 24.

Figure 3:
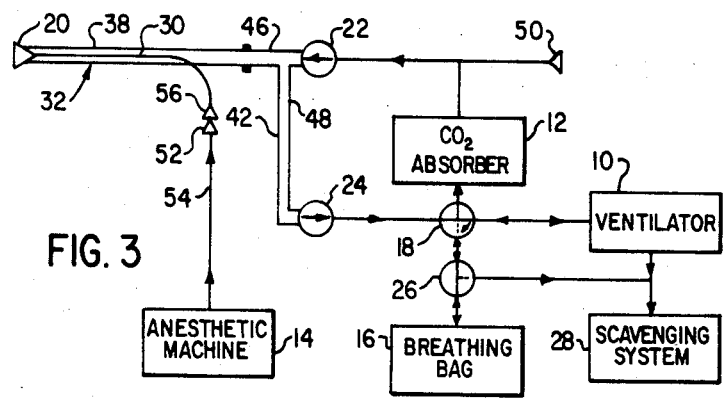
FIG. 3 is a block diagram showing how the circle configuration of FIG. 1 may be converted, in accordance with the invention, to the Bain circuit configuration.

(2) A circle-to-Bain circuit adaptor 42 (hereinafter described in greater detail) is connected between the outlet port of one-way valve 22 and the inlet port of one-way valve as shown in FIG. 3.

(3) Bain circuit outer (expiratory) hose 38 is connected to adaptor 42 as shown in FIG. 3.

(4) The fresh gas supply line of anesthetic machine 14 is disconnected from the inlet port of one way valve 22 and re-connected to Bain circuit inner (inspiratory) hose 30, thereby completing configuration of the Bain circuit. Note that the Bain circuit of FIG. 3 is otherwise identical to the circle circuit of FIG. 1.

In the Bain circuit of FIG. 3, during spontaneous respiration (i.e. when switch 18 is positioned to connect breathing bag 16 into the circuit) the patient, during inhalation, withdraws gas from the aforementioned "reservoir" in hose 38 and gas flows into the circuit from breathing bag 16, through $CO_2$ absorber 12 and valve 22 to equalize the pressure in the circuit. During positive pressure respiration (i.e. when switch 18 is positioned to connect ventilator 10 into the circuit) ventilator 10 forces gas into the patient's lungs from the aforementioned "reservoir" by pressurizing the circuit through $CO_2$ absorber 12, valve 22 and outer hose 38. Expiration is also a passive event in the Bain circuit of FIG. 3 during both spontaneous and positive pressure respiration; outer hose 38 merely acting to convey exhaled gas from the patient to adaptor 42 which, in turn, conveys the exhaled gas to valve 24 and thence to ventilator 10 (or breathing bag 16, depending upon the position of switch 18) or to scavenging system 28 if the circuit pressure causes valve 26 (or the corresponding valve in ventilator 10) to open. $CO_2$ absorber 12 need not be operative to remove carbon dioxide from the exhaled gas, since breathing gas is not recycled to the patient in the Bain circuit. Most of the exhaled gas passes to breathing bag 16 or ventilator 10 (depending upon the position of switch 18) or to scavenging system 28 if the circuit pressure is sufficient to open the exhaust valve. Adaptor 42 causes exhaled gases which pass through $CO_2$ absorber 12 to traverse a "mini circle" circuit comprising $CO_2$ absorber 12, one-way valves 22, 24 and adaptor 42.

Figure 4:
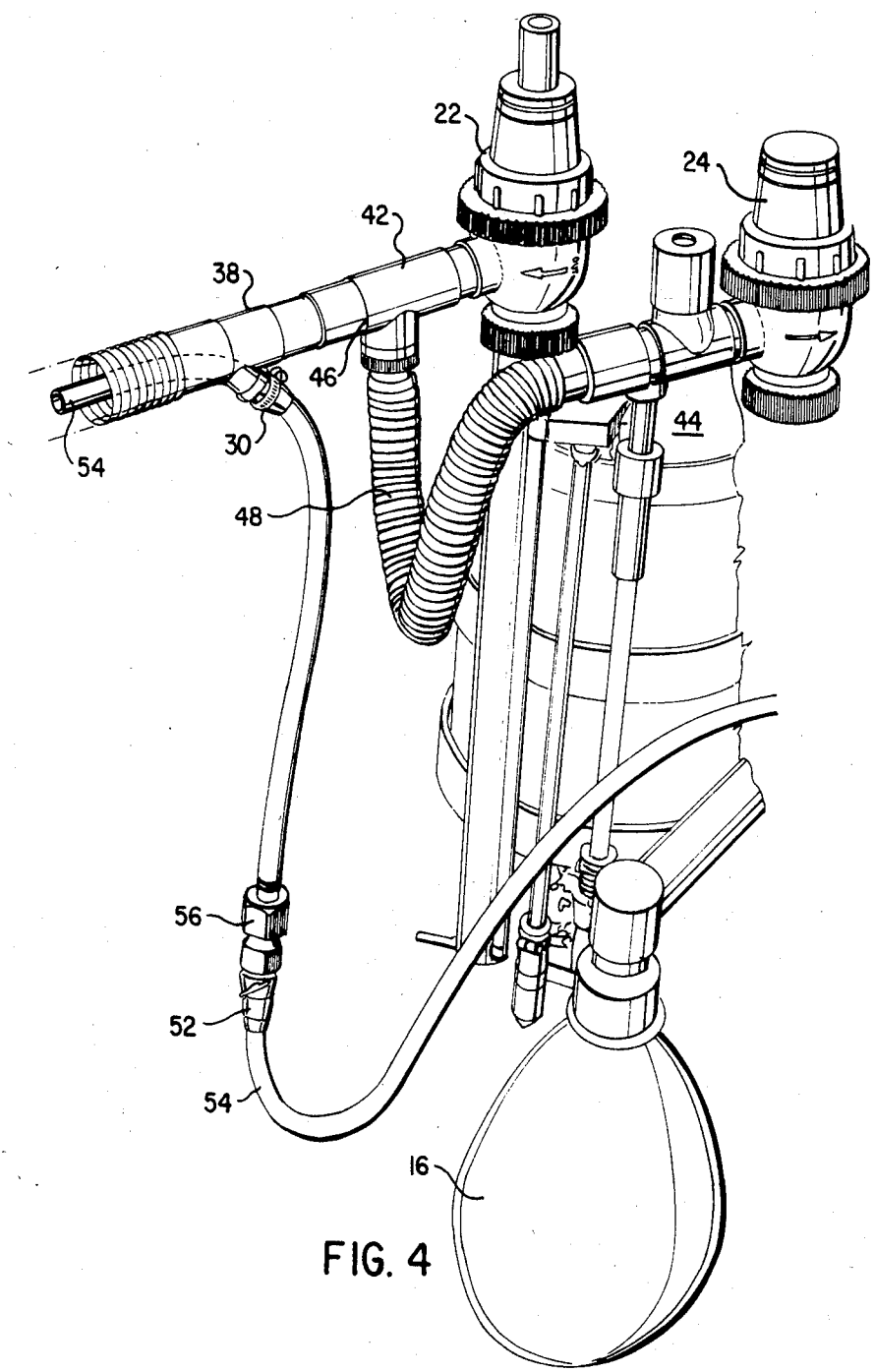
FIG. 4 is a pictorial illustration of a portion of the breathing circuit of FIG. 3, showing the adaptor of the preferred embodiment connected between the one-way valves of a typical circle circuit and connected to the coaxial Bain circuit breathing hoses.

Adaptor 42 is illustrated pictorially in FIG. 4, in which it appears connected between the outlet port of one way valve 22 and the inlet port 44 of a one way valve identical to one-way valve 24 described above, but not visible in FIG. 4. As may be seen in FIG. 4, adaptor 42 includes a "T" shaped portion 46, which is a conduit facilitating gas passage from the proximal end of Bain circuit outer hose 38 through flexible adaptor hose 48 to valve inlet 44 and also facilitating gas passage, during inspiration, from valve 22 through hose 38 to the patient.

The inlet port of the circle absorber system through which fresh gases are introduced from anesthetic machine 14 in the circle configuration of FIG. 1 must be occluded when the Bain circuit configuration of FIG. 3 is adopted. This is accomplished in the preferred embodiment by providing a valved coupler for coupling anesthetic machine 14 into the circle absorber system when the circle configuration of FIG. 1 is required. An ADEC quick disconnect 026-40/026-07 male/female valved coupler (the female half 50 of which appears schematically in FIG. 3 and the male half 52 of which can be seen in FIG. 4) is used in the preferred embodiment. Female half 50 is attached to the fresh gas inlet port of the circle absorber system with a short length of tubing interposed for convenience. Male half 52 is attached to a tube 54 (FIG. 4) which protrudes from the fresh gas outlet port of anesthetic machine 14. To configure the circle circuit of FIG. 1, male and female halves 52, 50 are coupled together, facilitating fresh gas passage from anesthetic machine 14 through valve 22. Connector halves 50, 52 together serve as a "control valve" for controlling the flow of fresh gas supplied to the circle circuit by anesthetic machine 14. When the Bain circuit configuration of FIG. 3 is required, coupler halves 50, 52 are separated, which action closes a valve in female half 50, thereby preventing loss of gas from the circle absorber system and facilitating pressurization of the Bain circuit by ventilator 10. A similar female connector 56 (FIG. 4) is swaged onto the fresh gas inlet port of Bain circuit inner hose 30 for mating with male connector half 52 coupled to anesthetic machine 14. Female connector half 56 is not valved, so as to prevent operation of the Bain circuit of FIG. 3 if anesthetic machine 14 is left connected to valve 22 instead of to hose 30 (the anesthetist would immediately detect the pressurization loss caused by leaving hose 30 open).

As indicated above, the Bain circuit is preferred in pediatric cases due to its relatively low resistance to normal patient breathing. In pediatric usage, the resistance of the "mini circle" portion of the breathing circuit must be borne by the smaller patient when breathing spontaneously. Although this has not proved to be a problem (since virtually all pediatric cases handled by the inventor are assisted or ventilated), caution is indicated. Furthermore, inspiratory resistance is not a problem with the Bain circuit, since fresh gas is delivered normally and the expiratory resistance of the "mini circle" provides a 1–3 cm. $H_2O$ expiratory retard, resulting in the patient breathing at a slightly higher lung volume which may prevent airway closure.

As will be apparent to those skilled in the art, in light of the foregoing disclosure, many alterations and modifications are possible in the practice of this invention without departing from the scope or spirit thereof. For example, hose 48 need not necessarily be flexible although configuration of the Bain circuit would likely be somewhat more difficult if adaptor 42 were of one-piece, rigid construction. Note also that adaptor 42 may be mounted with either leg of "T" portion 46 connected to valve 22. Further, although they are desirable, the quick disconnect couplers described above are not an essential feature of the invention. Accordingly, the scope of the invention is to be construed in accordance with the substance defined by the following claims.

I claim:

1. Apparatus for converting patient breathing equipment from a first circle circuit configuration to a second configuration, the first circle circuit configuration including a first one-way valve having an inlet for receiving gas from a source and an outlet for delivery of gas passing through the first valve, said first one-way valve outlet adapted to be connected to a first inspiratory conduit for carrying the gas from the first outlet of the first valve to the patient, a second one-way valve having an inlet and an outlet, said second one-way valve inlet adapted to be connected to a first expiratory conduit for receiving gas expired from the patient and delivering the received gas to the inlet of the second one-way valve, means connecting the outlet of the second one-way valve to the inlet of the first valve, pressure relief means connected between the outlet of the second one-way valve and the inlet of the first one-way valve for relieving overpressure, a first fresh gas supply conduit adapted to be coupled one-way the gas source leading into the inlet of the first one-way valve such that fresh gas is supplied to the first inlet, said coverting apparatus including means for blocking the first fresh gas supply conduit such that the patient breathing apparatus can be used in the second configuration, the second configuration including a second fresh gas supply conduit having a second fresh gas supply conduit outlet inlet for receiving fresh gas directly from a gas source and a second fresh gas supply conduit having means for delivery of such fresh gas to the patient, an inspiratory/expiratory conduit partially surrounding the second fresh gas supply conduit, the inspiratory/expiratory conduit having at one end thereof an exhaust gas outlet connected to the first one-way valve outlet; the inspiratory/expiratory conduit including means at the opposite end thereof for delivering fresh gas to a patient and for receiving gases expired by a patient, the opposite end of the inspiratory/expiratory conduit communicating with the second fresh gas supply conduit outlet, the inspiratory/expiratory conduit acting as a reservoir for storing fresh gas for delivery to the patient during inspiration and as a channel for exhausting exhaled gases during patient expiration, the apparatus further comprising a third conduit for coupling the exhaust gas outlet and the first one-way valve outlet to the second inlet of the second valve to the second inlet of the second valve whereby gas exhaled by a patient through the inspiratory/expiratory conduit passes through the exhaust outlet to the second inlet of the second one-way valve and also and gas emitted from the outlet of the first one-way valve passes to said inlet of the second one-way valve.

2. Apparatus as defined in claim 1, further comprising a control valve for automatically closing the first fresh gas supply conduit to shut off the flow of fresh gas in the first gas supply conduit to the inlet of said first valve upon conversion of the patient breathing equipment from the first to the second configuration.

3. A patient breathing apparatus comprising first and second one-way valves, each having respective inlets and outlets;
first conduit coupling means coupling the outlet of the first valve to the inlet of the second valve;
second conduit coupling means coupling the outlet of the second valve to the inlet of the first valve such that a circle is provided from the first valve outlet to the second valve inlet and from the second valve outlet to the first valve inlet;
means connected to said second conduit coupling means for relieving overpressure therein;
patient gas supply conduit means having inlet means for receiving gas from a gas source and outlet means for delivery of such gas to the patient;
patient inspiratory/expiratory conduit means partially surrounding the gas supply conduit means and having patient connection means at one end for delivering inspiratory gases to a patient and for receiving expired gases from a patient and having an exhaust gas outlet at its opposite end coupled to said first coupling means and thereby to the outlet of the first valve and the inlet of the second valve.

4. An apparatus according to claim 3 including a second gas supply conduit means coupled to the inlet of the first valve and a third valve means in said second gas supply conduit means for selectively closing the second gas supply conduit means.

5. A method for converting patient breathing equipment from a first circle circuit configuration to a second configuration, the first circle circuit configuration including a first one-way valve having an inlet for receiving gas from a source and an outlet for delivery of gas passing through the first valve, a first inspiratory conduit for carrying the gas from the outlet of the first valve to the patient, a second one-way valve having an inlet and an outlet, a first expiratory conduit for receiving gas expired from the patient and delivering the received gas to the inlet of the second valve, the an outlet of the second valve being coupled to the inlet of the first valve, a first fresh gas supply conduit coupling the gas source to the first inlet of the first valve such that fresh gas is supplied to the first inlet, the first fresh gas supply conduit being blocked when the patient breathing apparatus is in the second configuration, the second configuration including a second gas supply conduit having an inlet for receiving fresh gas directly from a gas source and an outlet for delivery of such fresh gas to the patient, an inspiratory/expiratory conduit partially surrounding the second gas supply conduit, the inspiratory/expiratory conduit having at one end thereof an exhaust gas outlet and means at the opposite end thereof for delivering fresh gas to a patient and for receiving gases expired by a patient, the opposite end of the inspiratory/expiratory conduit communicating with the outlet of said second gas supply conduit, the inspiratory/expiratory conduit comprising a reservoir for storing fresh gas for delivery to the patient during inspiration and a conduit for exhausting exhaled gases during patient expiration; the method comprising the steps of:
a. disconnecting the first inspiratory conduit and the first inspiratory conduit and the first expiratory conduit from the first and second valves
b. directly connecting the first outlet of the first valve to the second inlet of the second valve to permit gas communication therebetween;
c. connecting the exhaust outlet of the inspiratory/expiratory conduit to the second inlet of the second valve to permit gas communication therebetween; and
d. blocking the first gas supply conduit to prevent gases from flowing into the first valve inlet.

6. A method according to claim 5 including the step of disconnecting a source of fresh gas coupled to the first fresh gas supply conduit and thereby to the inlet of the first valve and reconnecting the source of fresh gas to the inlet of the second gas supply conduit; and
automatically closing the first fresh gas supply conduit upon disconnecting the source of fresh gas therefrom.

* * * * *